(12) United States Patent
Oguri et al.

(10) Patent No.: US 8,708,684 B2
(45) Date of Patent: Apr. 29, 2014

(54) DEVICE FOR MOLDING A DENTAL SHADE GUIDE

(75) Inventors: Makoto Oguri, Tsukuba (JP); Hironobu Akizumi, Tsukuba (JP)

(73) Assignee: Tokuyama Dental Corporation (JP)

( * ) Notice: Subject to any disclaimer, the term of this patent is extended or adjusted under 35 U.S.C. 154(b) by 316 days.

(21) Appl. No.: 13/220,735

(22) Filed: Aug. 30, 2011

(65) Prior Publication Data

US 2012/0056343 A1  Mar. 8, 2012

(30) Foreign Application Priority Data

Sep. 2, 2010 (JP) ................. 2010-197066

(51) Int. Cl.
*B29C 39/18* (2006.01)
*B29C 35/08* (2006.01)

(52) U.S. Cl.
USPC ........ 425/174.4; 425/127; 264/275; 264/494; 264/496

(58) Field of Classification Search
None
See application file for complete search history.

(56) References Cited

U.S. PATENT DOCUMENTS

| 4,618,325 A | * | 10/1986 | Appelle | 433/26 |
| 4,810,193 A | * | 3/1989 | Wieder | 433/26 |
| 5,149,267 A | * | 9/1992 | Longhini et al. | 433/26 |
| 6,994,808 B2 | * | 2/2006 | Lee et al. | 264/1.21 |

FOREIGN PATENT DOCUMENTS

| EP | 1609438 | * | 12/2005 |
| JP | 2004-203865 A | | 7/2004 |
| JP | 1242228 | | 6/2005 |
| JP | 2007014375 | * | 1/2007 |
| WO | WO 8808285 | * | 11/1988 |

* cited by examiner

*Primary Examiner* — Edmund H. Lee
(74) *Attorney, Agent, or Firm* — Skinner and Associates

(57) ABSTRACT

In dental crown restoration, a dental shade guide which is selected to match patient's teeth comprises a shade-guide portion and a handle. A molding device for molding the dental shade guide comprises a molding plate having a shade-guide molding portion and a handle-holding groove. The molding plate is closed by a cover. While the handle is held in the handle-holding groove of the molding plate, dental composite resin paste is filled in the shade-guide molding portion and the upper surface of the molding plate is tightly pressed by the inner surface of the cover.

6 Claims, 5 Drawing Sheets

DEVICE FOR MOLDING A DENTAL SHADE GUIDE

BACKGROUND OF THE INVENTION

The present invention relates to a device for molding a dental shade guide and in particular to a device for molding a shade guide used for determining dental composite resin paste closest to the shade of natural teeth of a dental patient, the shade guide being molded from dental composite resin paste actually used for restoration of the natural teeth. The present invention also relates to a method of molding the shade guide by the molding device.

Recently, in dental restoration when a natural tooth is partially lost in an oral cavity of a dental patient, in order to improve aestheticity of the partially-lost natural tooth to be restored or an artificial tooth substituted for the natural tooth, a number of shade guides are prepared. By comparing the shade guides arranged in order of density with the shade of natural teeth of the patient, the shade guide that match the natural teeth in shade is determined as disclosed in U.S. Pat. No. 5,149,267B1. The photo-curable composite resin paste is prepared based on selected shade guide as disclosed in JP2004-203865A.

Specifically, in order to select the shade of the composite resin paste, as shown in FIG. 5, a shade guide 101 for selecting the shade of composite resin paste comprises a shade guide portion 102 which is compared in shade with the front face of a natural tooth, and a handle 103 integrally molded with the shade guide portion 102 like a rod by a mold (not shown) in Japanese Design No. 1242228.

The shade guides 101 in Japanese Design No. 1242228 are arranged circumferentially of a round plate 105 forming a shade guide holder 104 in order of density.

In the round plate 105, there is a plurality of guide grooves 106 extending radially at regular intervals circumferentially. An inner edge 106a of the guide groove 106 engages in an engagement groove 106a on each side of the handle 103 to make the handle 103 slide radially inward, so that the shade guide 101 is detachably disposed.

On the rear side of a shade guide portion 102 of the shade guide 101, there is a projection 102a which engages in an inner hole of two holes 107 disposed on an extended line of the guide groove 106 of the round plate 105.

In FIG. 5, in the middle on the front side of the handle 103 of the shade guide 101, there is formed a concave finger-contacting portion 103b on which a thumb is applied to allow the shade-guide portion 102 of the shade guide 101 to slide by pressing out of the guide groove 106, so that the projection 102a engages on the outer hole 107.

Thus, the shade-guide portion 102 of the shade guide 101 is kept to project from the outer circumference in FIGS. 6 and 7 thereby preventing dropping the selected shade guide 101 out of the round plate 105 unintentionally.

In FIG. 6, while the patient's mouth opens, the shade guide portion 102 of the shade guide 101 on the outer circumference of the round plate 105 gets close to a natural tooth to be restored or adjacent teeth. While grasping the center of the round plate 105 with one hand, the round plate 105 turns clockwise or counterclockwise with the other hand as shown by an arrow in FIG. 6. By comparing a front side 102a of the shade guide portion 102 in shade with the natural tooth, the shade guide 101 closest to the natural tooth to be restored or adjacent teeth is determined.

The selected shade guide 101 ensures the shade of dental composite resin paste.

The shade guide 101 disposed in the shade guide holder 104 is limited to about ten in number, and colored industrial plastic material is used as the shade guide 101. The adjacent shade guides 101 differ from each other in shade greatly and its texture is poor compared with natural teeth. It is likely to cause difference in shade not only in the shade guide 101 selected by the shade of a natural tooth to be restored but also in composite resin paste selected by the shade guide 101.

Common composite resin is likely to change in shade with a production lot. Before and after curing, its shade is likely to differ slightly. Thus, the composite resin paste selected with the shade guide 101 differs in shade from patient's teeth after restored.

Furthermore, as shown in FIG. 5, the front face of the shade guide portion 102 of the shade guide 101 is tilted so that light is uniformly reflected, while the concave front face of a natural tooth is likely to cause diffused reflection of light. Even if the shade guide 101 is identified in shade with the natural tooth, the cured composite resin determined by the shade could subtly differ from the natural tooth.

In order to produce the shade guide as above, for example, a handle is separately molded and photo-curable paste-like dental composite resin is supplied on the upper end of the handle like a tooth shape. The composite resin is cured by radiating light to form the glossy shade guide 102 close to natural teeth.

However, the shade guide portion has an uneven surface. When light is radiated to the dental composite resin paste filled in a mold to cure the composite resin paste, the surface in an opening of the mold comes in contact with air to form an uncured or unpolymerized layer which has to be removed by grinding to make the surface of the shade guide portion smooth.

SUMMARY OF THE INVENTION

In view of the disadvantages, it is an object of the invention to provide a device for molding a dental shade guide used for determining dental composite resin paste closest to the shade of natural teeth of a dental patient, the shade guide being molded from dental composite resin paste actually used for restoration of the natural teeth.

BRIEF DESCRIPTION OF THE DRAWINGS

It is another object of the invention to provide a method of molding the dental shade guide using the molding device as above.

BRIEF DESCRIPTION OF THE DRAWINGS

Figure 1:
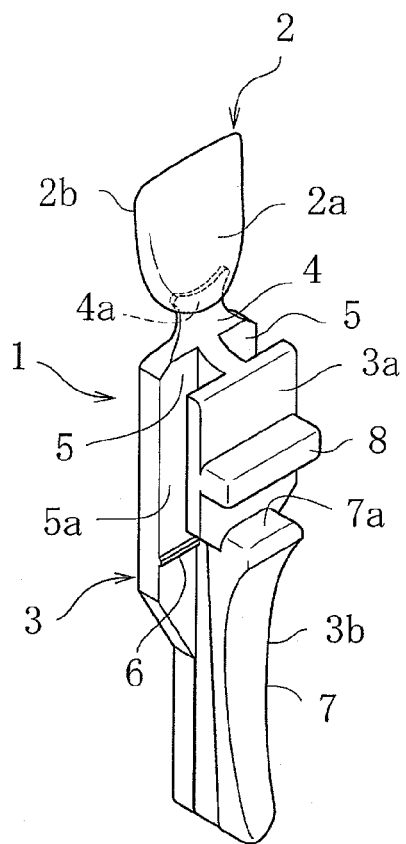

FIG. 1 is a perspective view of a dental shade guide molded by a molding device according to the present invention.

Figure 2:
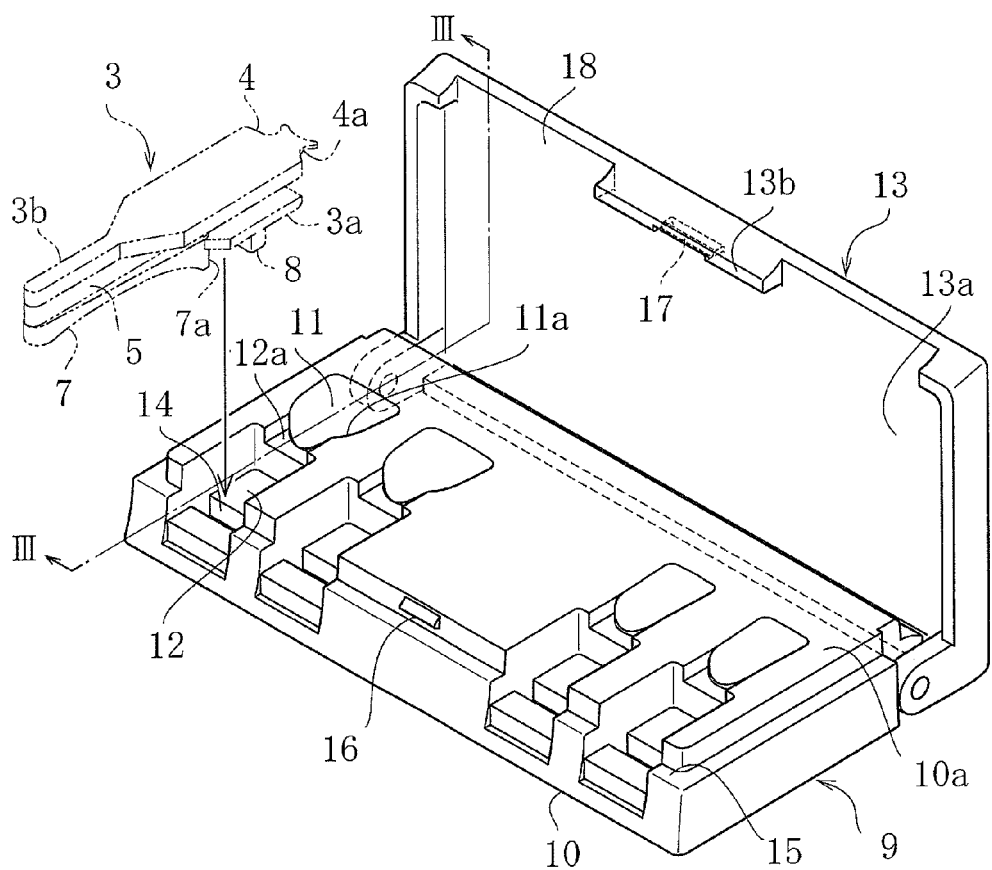

FIG. 2 is a perspective view of the molding device that is open.

Figure 3:
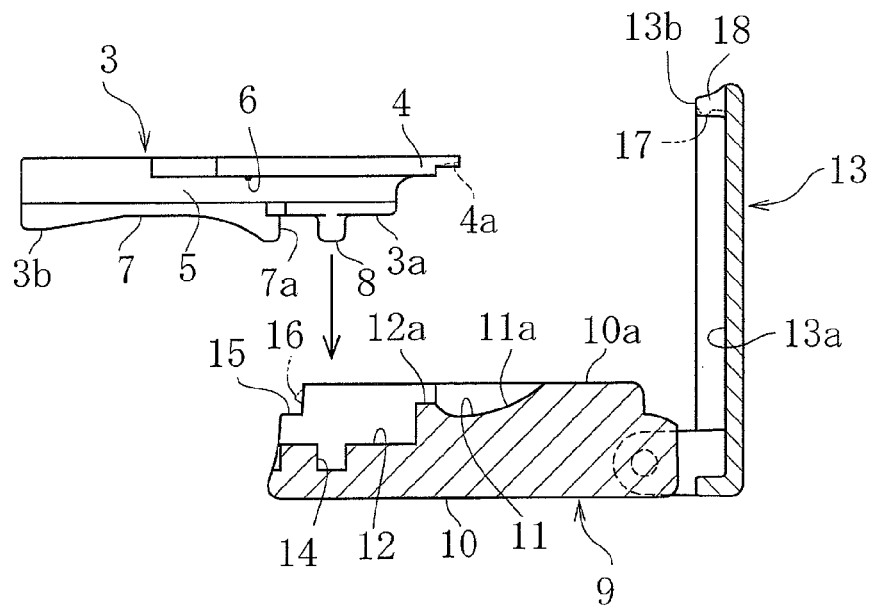

FIG. 3 is a vertical sectional side view taken along the line III-III in FIG. 2 to show how to put a handle of the dental shade guide on the molding device.

Figure 4:
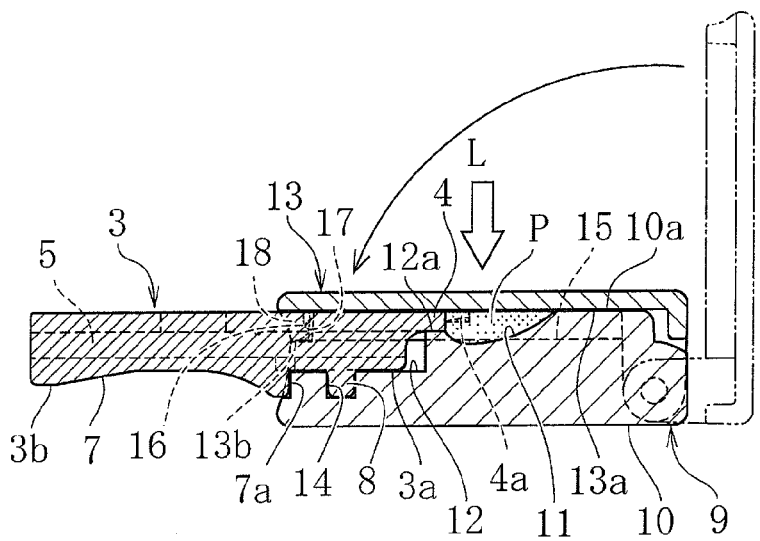

FIG. 4 is a vertical sectional side view to show the molding device closed after dental composite resin is filled, with the handle of the dental shade guide disposed in the molding device.

Figure 5:
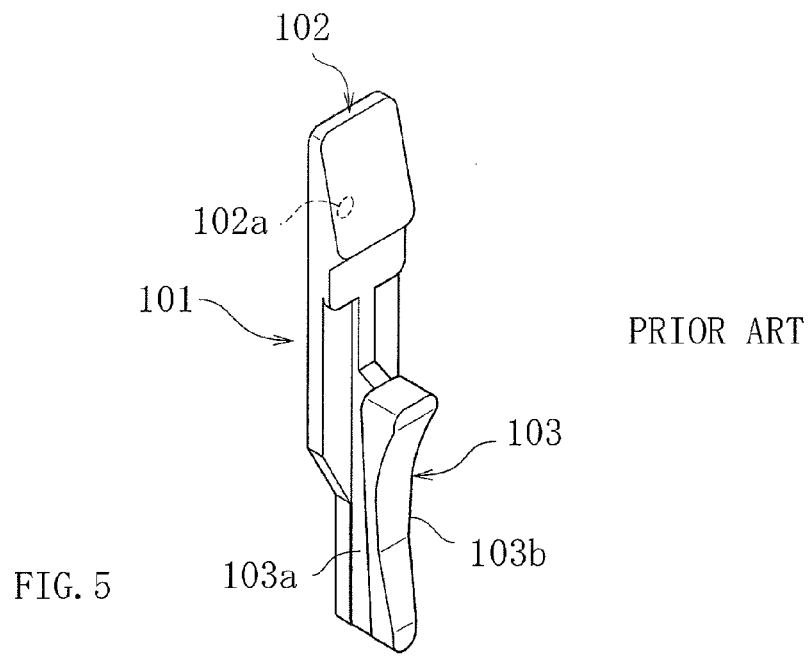

FIG. 5 is a perspective view of a conventional shade guide.

Figure 6:
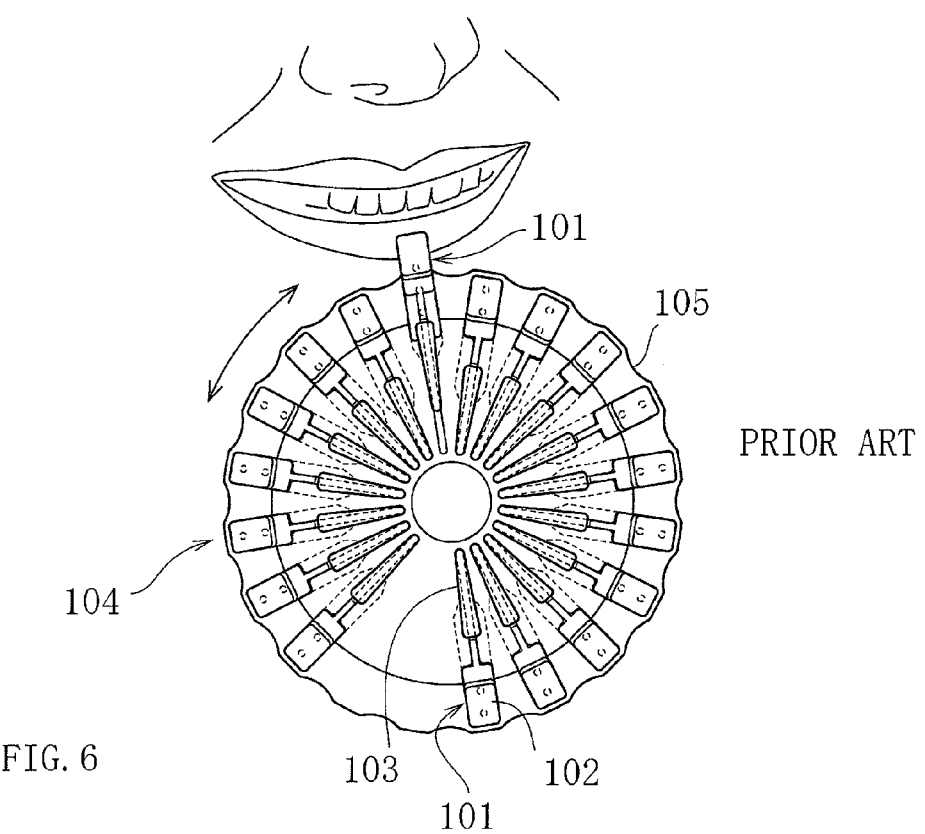

FIG. 6 is a schematic view showing how to use the conventional shade guide.

Figure 7:
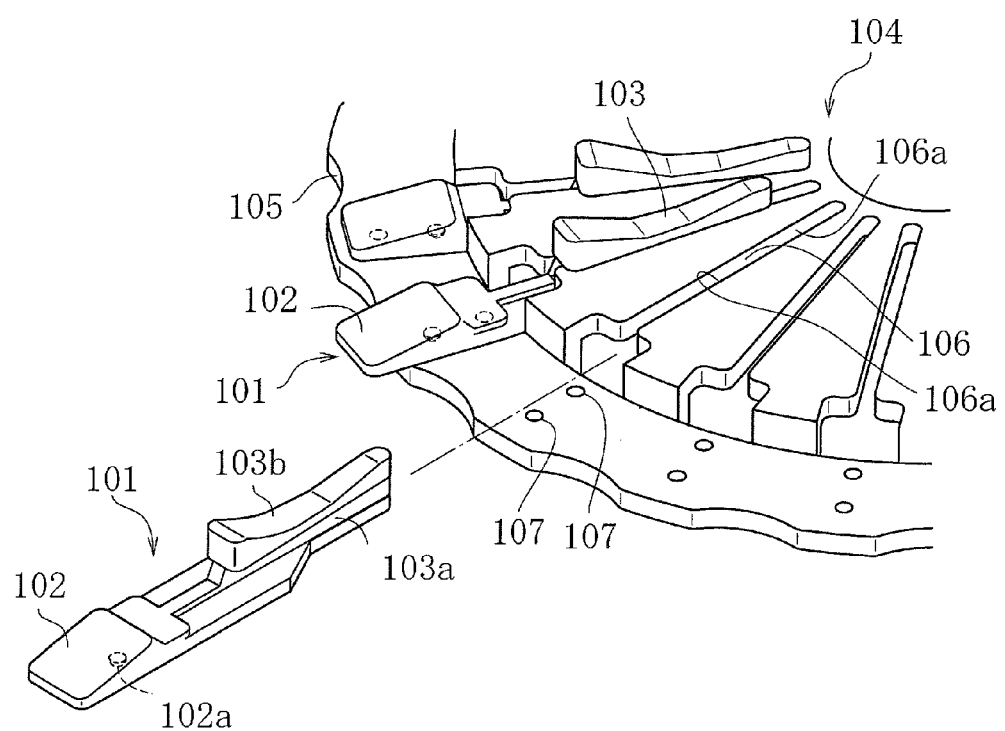

FIG. 7 is a perspective view showing how to insert the conventional shade guide into a round plate.

DETAILED DESCRIPTION OF PREFERRED EMBODIMENT

In FIG. 1, dental shade guides 1 comprise a shade guide portion 2 for comparing a plurality of shades to select a suitable one from the shades, and a handle 3 for supporting the shade guide portion 2.

The shade guide portion 2 comprises a front face 2a and a back face 2b both having the same shade as a natural tooth requiring restoration in a dental patient or adjacent teeth. The front face 2a is convex like the front face of a natural tooth and the back face 2b is plain.

The handle 3 for supporting the shade guide portion 2 is made of industrial plastic material by a different mold (not shown).

An upper end 4 of an upper half 3a of the handle 3 tapers, and an end face 4a of the upper end 4 is concave. When the shade guide portion 2 is molded by a molding device 9 according to the present invention later described, the shade guide portion 2 is integrally formed with the end face 4a.

An engagement groove 5 is formed in each side of the handle 3, and a projection 6 is formed on one of inner surface facing each other of the engagement groove 5.

Like the conventional shade guide 104 in FIGS. 6 and 7, the shade guide 1 can be stored in a plurality of guide grooves 106 radially formed at regular intervals circumferentially in the round plate 105. When the engagement groove 5 of the shade guide 1 is in contact with the inner edge 106a of the guide groove 106, the projection 6 is pressed by the inner side edge 106a of the guide groove 106 to increase radial sliding resistance of the shade guide 1 so that the shade guide portion 2 is held to project from the outer circumference of the round plate 105.

In FIG. 1, on the front face of the handle 3 of the shade guide 1, a concave finger-contacting portion 7 is formed and a positioning protrusion 8 projects above the upper end 7a of the finger-contacting portion 7.

In order to draw the shade guide portion 2 of the shade guide 1 out of the guide groove 106 of the round plate 105, a thumb is put on the finger-contacting portion 7 to enable the shade guide 1 to be pushed out.

In FIG. 2, the molding device 9 for molding the shade guide 1 comprises a rectangular molding plate 10; a plurality of shade-guide molding portions 11 having two pairs of different size, each of the plurality of shade-guide molding portions 11 having a bottom 11a for molding the front face 2a of the shade-guide portion 2 of the shade guide 1 such that a photo-curable composite resin paste P is filled in the bottom 11a; a plurality of handle-holding groove 12 each of which communicates with the bottom 11a so that the upper half 3a of the handle 3 of the shade guide 1 formerly molded is held in the handle-holding groove 12; and a light-permeable cover 12 that covers an upper surface 10a of the molding plate 10.

When the molding plate 10 is covered with the cover 13, the upper surface of the molding plate 10 is placed within the same plane as the inner surface 13a of the cover 13 facing the upper surface 10a and is formed as smooth surface. Only the portion of the inner surface 13a of the cover 13 which faces the shade-guide molding portion 11 of the molding plate 10 may be placed within the same plane as the upper surface 10a of the molding plate 10.

The inner surface 13a of the cover 13 may partially project in the shade-guide molding portion 11 in the upper surface 10a of the molding plate 10, and the other portion of the inner surface 13a may be placed within substantially the same plane as the upper surface 10a of the molding plate 10.

The smooth surface in the present invention means that surface roughness shown by arithmetic mean roughness (Ra) determined under ISO 4287 1997(JIS B0601) is not more than 10 μm, preferably, not more than 1 μm.

The bottom 11a of the shade-guide molding portion 11 may preferably be formed like a curved surface corresponding to the front shape of a natural tooth of the patient, or like a curved surface such that the front face 3a of the shade guide portion 2 is formed after molding as shown in FIG. 1.

UV coating may preferably be applied to the bottom 11a of the shade-guide molding portion 11 and the inner surface 13a of the cover 13 so that the bottom 11a and the inner surface 13a may be flat and so that the cured composite resin may leave the bottom 11a and the inner surface 13a readily.

As mentioned later, in the molding device 9, the handle 3 of the shade guide 1 is held in the handle-holding groove 12 of the molding plate 10. When the composite resin paste P is filled in the bottom 11a of the shade-guide molding portion 11, the composite resin paste P exposed from the upper surface 10a of the shade-guide molding portion 11 is tightly pressed by the inner surface 13a of the cover 13 in the shade-guide molding portion 11.

When the handle 3 is held in the handle-holding groove 12 in the upper surface 10a of the molding plate 10, as shown by a dot-dash line in FIG. 2, the handle 3 is reversed such that the front face of the handle 3 faces the handle-holding groove 12, and the upper half 3a is held in the handle-holding groove 12 while a lower half 3b projects outside.

The handle-holding groove 12 comprises an end-positioning groove 12a and a positioning groove 14. The end-positioning groove 12a is formed at a border with the bottom 11a of the shade-guide molding portion 11, and the positioning groove 14 engages with the positioning protrusion 8 on the upper half 3a when the upper half 3a of the handle 3 is held in the handle-holding groove 12.

On the outer periphery of the upper surface 10a of the molding plate 10, there is formed a engagement step 15 which engages with an outer periphery 13b of the cover 13 when the molding plate 10 is covered with the cover 13. In the middle of the front of the engagement step 15, a lower engagement projection 16 is formed.

An upper engagement projection 17 in the middle of the outer periphery 13b engages with the lower engagement projection 17 when the molding plate 10 is covered with the cover 13.

On the outer periphery 13b of the cover 13, there is formed a recess 18 corresponding to the handle-holding groove 12 in which the handle 3 is put reversely.

The recess 18 prevents the handle 13 from obstructing the closed cover 13 when the handle 3 is disposed in the handle-holding groove 12 of the molding plate 10.

Then, the shade guide 1 will be molded using the molding device 9 with respect to FIGS. 3 and 4.

At the examination, a dentist oneself prepares a plurality of containers each of which contains a photo-curable composite resin paste having a desired shade.

As shown in FIG. 3, the handle 3 is reversely put into the handle-holding groove 12 of the molding plate 10, and the positioning projection 8 on the front face of the handle 3 is engaged in the positioning groove 14 of the handle-holding groove 12. An end face 10 of the finger-contacting portion 7 comes in contact with the front face of the molding plate 10, and the front end of the molding plate 10 is held between the positioning projection 8 and the finger-contacting portion 7 to allow the handle 7 to be held.

The end face 4a of the upper end portion 4 of the handle 3 is disposed in the shade-guide molding portion 11, and the surface of the upper half 3a facing the inner surface 13a of the cover 13 is coplanar with the upper surface 10a of the molding plate 10.

The surface of the upper end portion 4 facing the inner surface 13a of the cover 13 is placed lower than the upper surface 10a of the molding plate 10 as a step. Into the step, the dental composite resin paste P flows from the shade-guide molding portion 11 when molded.

After the dental composite resin paste P is filled in the shade-guide molding portion 11 of the molding plate 10 from the container containing the composite resin paste, the upper surface 10a of the molding plate 10 is covered with the cover 13.

The upper engagement projection 17 of the cover 13 elastically engages with the lower engagement projection 16 of the molding plate 10, so that the upper surface 10a of the molding plate 10 is tightly in contact with the inner surface 13a of the cover 13. Simultaneously, the upper surface of the composite resin paste P exposed from the shade-guide molding portion 11 is tightly pressed by the inner surface of the cover 13.

Then, light L is radiated through the light-permeable cover 13 from the outside of the molding plate 10 toward the shade-guide molding portion 11 in which the composite resin paste P is filled, so that the composite resin paste P is cured and released.

In FIG. 1, the shade guide 1 in which the shade-guide portion 2 is integrally formed with the handle 3 is molded.

The operation is applied to a plurality of dental composite resin pastes. The shade guides 1 thus obtained are arranged in order of density and stored in the round plate 105 of the shade guide holder 104.

The shade guide 1 may preferably be molded for a production lot for a new dental composite resin and stored in the round plate 105 of the shade guide holder 104.

The foregoing merely relates to an embodiment of the invention. Various changes and modifications may be made by a person skilled in the art without departing from the scope of claims wherein:

What is claimed is:

1. A device for molding a dental shade guide comprising a shade-guide portion for selecting shade and a handle supporting the shade-guide portion, the device comprising:
    a molding plate having a shade-guide molding portion on an upper surface and a handle-holding groove communicating with the shade-guide molding portion to hold the handle of the dental shade guide; and
    a light-permeable cover that is adapted to close over the molding plate and has an inner surface facing the molding plate, photo-curable composite resin paste being filled in the shade-guide molding portion while the handle of the dental shade guide is held in the handle-holding groove, the shade-guide molding portion being tightly pressed by the inner surface of the cover when the molding plate is closed by the cover.

2. The device of claim 1 wherein the inner surface of the cover is positioned within substantially the same plane as the upper surface of the molding plate when the molding plate is closed by the cover.

3. The device of claim 1 wherein the inner surface of the cover slightly projects into the shade-guide molding portion when the molding plate is closed by the cover.

4. The device of claim 1 wherein a bottom of the shade-guide molding portion is formed to match a front face of a natural tooth.

5. The device of claim 4 wherein the bottom of the shade-guide molding portion has a smooth surface having arithmetic mean roughness of not more than 10 μm as measured by ISO 4287.

6. The device of claim 1 wherein the inner surface of the cover has a smooth surface having arithmetic mean roughness of not more than 10 μm as measured by ISO 4287.

* * * * *